United States Patent [19]

Bouscuet et al.

[11] Patent Number: 4,458,074

[45] Date of Patent: Jul. 3, 1984

[54] PROCESS FOR THE PREPARATION OF 5,6,7,7A-TETRAHYDRO-4H-THIENO[3,2-C]PYRIDIN-2-ONES

[75] Inventors: André Bouscuet; Alain Heymès, both of Sisteron, France

[73] Assignee: Sanofi, Toulouse, France

[21] Appl. No.: 393,381

[22] Filed: Jun. 29, 1982

[30] Foreign Application Priority Data

Jun. 30, 1981 [FR] France ................ 81 13067

[51] Int. Cl.³ .......................................... C07D 495/04
[52] U.S. Cl. ................................................. 546/114
[58] Field of Search ........................................ 546/114

[56] References Cited

U.S. PATENT DOCUMENTS 4,127,580 11/1978 Braye ................................. 546/114

FOREIGN PATENT DOCUMENTS 53950 6/1982 France .

Primary Examiner—Henry R. Jiles
Assistant Examiner—Bernard Dentz
Attorney, Agent, or Firm—Weiser & Stapler

[57] ABSTRACT

The present invention provides a process for the preparation of 5,6,7,7a-tetrahydro-4H-thieno[3,2-c]-pyridin-2-ones of the general formula:

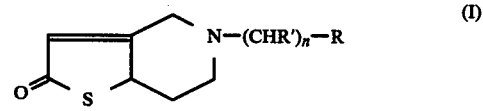

in which R is a hydrogen atom or a phenyl radical optionally substituted by at least one halogen atom, lower alkyl radical, lower alkoxy radical, nitro group, carboxyl group or alkoxycarbonyl radical, R' is a hydrogen atom or lower alkyl radical and n is 0 or a number of from 1 to 4, wherein a compound of the general formula:

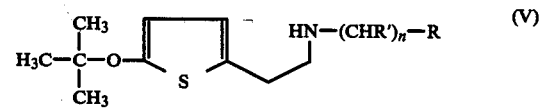

in which R, R' and n have the same meanings as above, is reacted with formaldehyde to give a compound of the general formula:

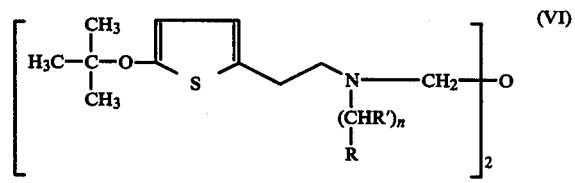

in which R, R' and n have the same meanings as above, whereafter this compound is treated with dry hydrogen chloride to give the desired compound of general formula (I). The compounds are useful as anti-thrombotic agents.

6 Claims, No Drawings

PROCESS FOR THE PREPARATION OF 5,6,7,7A-TETRAHYDRO-4H-THIENO[3,2-C]PYRIDIN-2-ONES

The present invention is concerned with a new process for the preparation of 5,6,7,7a-tetrahydro-4H-thieno[3,2-c]pyridin-2-ones.

The 5,6,7,7a-tetrahydro-4H-thieno[3,2-c]pyridin-2-ones with which the present invention is concerned are compounds of the general formula:

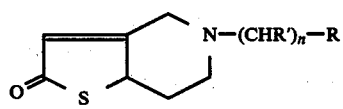
(I)

wherein R is a hydrogen atom or a phenyl radical optionally substituted by at least one halogen atom, lower alkyl radical, lower alkoxy radical, nitro group, carboxyl group or alkoxycarbonyl radical, R' is a hydrogen atom or a lower alkyl radical and n is 0 or a number of from 1 to 4.

These compounds possess platelet anti-aggregant properties and anti-thrombotic properties, the therapeutic use of which is the subject matter of our French patent application Nos. 8025274; 8025275 and 8025276.

However, the processes described in the three above-mentioned French patent applications do not permit high yields to be obtained when operating on a large scale.

It is an object of the present invention to provide a simple process which is easy to carry out and which gives higher overall yields than the processes previously known for preparing these compounds of general formula (I).

French patent specification No. 75 23 786 describes a process for obtaining thienopyridine derivatives of the general formula:

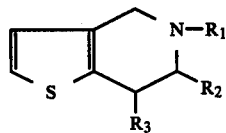
(II)

in which $R_1$ is an optionally substituted alkyl, aryl or aralkyl radical and $R_2$ and $R_3$ are hydrogen atoms or lower alkyl, aryl or heterocyclic radicals, by the cyclisation in two stages of compounds of the general formula:

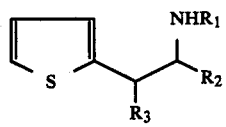
(III)

in which $R_1$, $R_2$ and $R_3$ have the same meanings as above; and French patent specification No. 8,025,276 describes the transformation of compounds of the general formula:

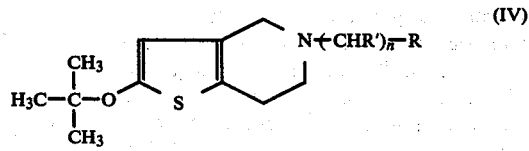
(IV)

in which R', R and n have the same meanings as in general formula (I), into compounds of general formula (I) by heating at a temperature of from 80° to 180° C. in the presence of a mineral or organic acid.

We have now found, and this is the subject of the present invention, that when applying the conditions used for obtaining compounds of formula (II) from compounds of general formula (III) to compounds of the general formula:

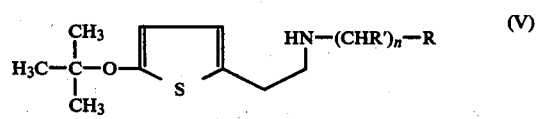
(V)

in which R, R' and n have the same meanings as above, the compounds of general formula (I) are unexpectedly obtained directly under less severe conditions, especially with regard to the temperature, and in satisfactory yields.

Thus, according to the present invention, in order to obtain a compound of general formula (I):

(a) a compound of general formula (V) is reacted with formaldehyde in an aqueous medium at ambient temperature and with vigorous stirring to give a reaction product which is presumed to have the general formula:

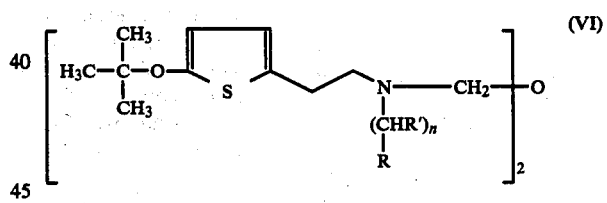
(VI)

in which R, R' and n have the above-given meanings, and (b) this reaction product (VI) is reacted in a second stage with an anhydrous solution of hydrogen chloride in a polar, aprotic solvent.

More particularly, it is essential that the product of the addition of the formaldehyde (the formaldehyde being used in 1 to 5 times the stoichiometrical amount) to the compound of general formula (V) is isolated and obtained free from water. However, it may be used in the following stage in solution in an inert solvent, for example an aromatic hydrocarbon, such as benzene or toluene, or in a halogenated solvent, such as methylene chloride, or some other similar solvent which is compatible with the nature of the product, the essential point being that the solvent is anhydrous.

The product obtained in stage (a) is poured into an anhydrous solution of hydrogen chloride in a polar, aprotic solvent, preferably dimethylformamide. However, other solvents of a similar nature may be used, such as dimethyl sulphoxide, N-methylpyrrolidone, N,N-dimethylacetamide or the like.

Generally, the hydrogen chloride is used in a stoichiometrically equivalent amount but it may be used in an excess of up to 100% of this equivalent amount. The reaction is usally carried out at a temperature of from −20° to 50° C. and preferably of from 0° to 30° C.

The compounds of general formula (I) thus obtained may subsequently be isolated and purified by conventional methods. In order to perform these operations, it is advantageous to convert the free bases of general formula (I) into their salts, for example into their acid-addition salts, by reaction with mineral or organic acids. The compounds of general formula (I) can subsequently be liberated from the salts in conventional manner.

The following Example is given for the purpose of illustrating the present invention:

EXAMPLE

Preparation of 5-(2-chlorobenzyl)-5,6,7,7a-tetrahydro-4H-thieno[3,2-c]pyridin-2-one hydrochloride.

(a) 12.94 g. (0.04 mole) N-(o-chlorobenzyl)-2-[5-tert.-butoxy-(thienyl-2)]-ethylamine are added, with vigorous stirring and while maintaining the temperature at 20° C., to 14 g. (0.16 mole) of an aqueous 35% by weight solution of formaldehyde. When the addition is finished, the reaction mixture is further stirred for 15 minutes, after which 15 ml. methylene chloride are added thereto. The organic phase is isolated, washed with an aqueous solution of sodium chloride and dried over anhydrous sodium sulphate.

(b) The solution thus obtained is added with stirring and while maintaining a temperature of from 20° to 25° C. to 8.25 ml. of a 4.85 N solution of gaseous hydrogen chloride in dimethylformamide. After further stirring for 20 minutes, the reaction mixture is added to 48 ml. of a 1 N aqueous solution of sodium bicarbonate. The organic phase is isolated and then evaporated in vacuo at a temperature of less than 60° C. The oily residue obtained solidifies upon triturization with 20 ml. ethanol. After filtering and drying, there are thus obtained 5.8 g. of 5-(2-chlorobenzyl)-5,6,7,7a-tetrahydro-4H-thieno[3,2-c]pyridin-2-one in the form of crystals. The yield is 52% of theory; m.p. 73° C.

NMR (CDCl$_3$): 7.1–7.6 (m,4H); 6.2 (s,1H); 4.2–4.7 (m,1H); 3.9 (s,2H); 1.5–4.2 (m,6H).

The corresponding hydrochloride hemihydrate melts, with decomposition, at 180° C.

We claim:

1. A process for the preparation of a 5,6,7,7a-tetrahydro-4H-thieno [3,2-c]pyridin-2-one of the formula:

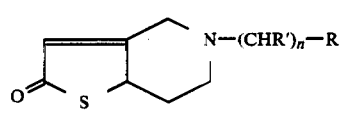

in which R is a hydrogen atom, phenyl, or phenyl substituted by at least one halogen atom, lower alkyl radical, lower alkoxy radical, nitro group, carboxyl group or alkoxycarbonyl radical, R' is a hydrogen atom or lower alkyl radical, and n is 0 or an integer of from 1 to 4, which comprises reacting a compound of the formula:

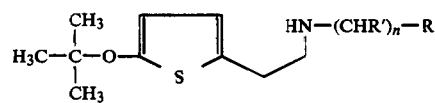

in which R, R' and n are as hereinbefore described, with formaldehyde, and then treating the resulting compound with dry hydrogen chloride.

2. A process according to claim 1, wherein the reaction between a compound of the formula (V) and formaldehyde is carried out at ambient temperature.

3. A process according to claim 1 or 2, wherein the reaction of the product of the first step with hydrogen chloride is carried out in an anhydrous medium.

4. A process according to claim 3, wherein the reaction is carried out in a polar, aprotic solvent.

5. A process according to claim 4, wherein the solvent is selected from the group consisting of dimethylformamide, dimethyl sulphoxide, N-methylpyrrolidone and N,N-dimethylacetamide.

6. A process according to claim 1 wherein the initial compound is N-(O-chlorobenzyl)-2-[5-tert.-butoxy-(thienyl-2)]-ethylamine and 5-(2-chlorobenzyl)-5,6,7,7a-tetrahydro-4H-thieno[3,2-c]-pyridin-2-one hydrochloride is prepared.